United States Patent

Bowman et al.

[11] Patent Number: 5,832,592
[45] Date of Patent: Nov. 10, 1998

[54] METHOD OF MAKING A RESPIRATION SENSOR

[75] Inventors: Bruce Bowman, Eden Prairie; Peter Stasz, St. Paul, both of Minn.

[73] Assignee: Edentec, Inc., Eden Prairie, Minn.

[21] Appl. No.: 936,491

[22] Filed: Sep. 19, 1997

Related U.S. Application Data

[63] Continuation of Ser. No. 685,210, Jul. 23, 1996, abandoned, which is a continuation of Ser. No. 390,929, Feb. 17, 1995, abandoned, which is a continuation of Ser. No. 201,045, Feb. 24, 1994, abandoned, which is a continuation of Ser. No. 934,725, Aug. 24, 1992, abandoned, which is a division of Ser. No. 665,552, Mar. 5, 1991, Pat. No. 5,161,541.

[51] Int. Cl.[6] .............................. H01C 7/02; H01C 17/06; B05D 5/12
[52] U.S. Cl. .............................. 29/612; 29/620; 427/96; 338/22 R
[58] Field of Search .......................... 29/612, 620; 427/96; 128/724, 725; 338/22 R

[56] References Cited

U.S. PATENT DOCUMENTS

| | | | |
|---|---|---|---|
| 3,766,908 | 10/1973 | Haynes | 128/2 H |
| 3,903,876 | 9/1975 | Harris | 128/2.08 |
| 3,906,936 | 9/1975 | Habal | 128/2 R |
| 3,916,877 | 11/1975 | Beckman | 128/2.05 R |
| 3,962,917 | 6/1976 | Terada | 73/204 |
| 3,999,537 | 12/1976 | Noiles | 128/724 |
| 4,036,211 | 7/1977 | Veth et al. | 128/2 R |
| 4,146,957 | 4/1979 | Toenshoff | 427/376.3 |
| 4,176,660 | 12/1979 | Mylrea et al. | 128/724 |
| 4,278,706 | 7/1981 | Barry | 29/620 |
| 4,464,646 | 8/1984 | Burger et al. | 338/22 R |
| 4,536,274 | 8/1985 | Papadakis et al. | 427/124 |
| 4,555,414 | 11/1985 | Hoover et al. | 427/96 |
| 4,756,756 | 7/1988 | Cassat | 427/96 |
| 4,818,827 | 4/1989 | Ipcinski et al. | 427/96 |
| 4,907,341 | 3/1990 | Chapel, Jr. et al. | 29/612 |
| 4,923,401 | 5/1990 | Marshall et al. | 434/22 |
| 5,081,866 | 1/1992 | Ochiai et al. . | |
| 5,100,695 | 3/1992 | Kawakami et al. | 427/96 |
| 5,131,399 | 7/1992 | Sciarra | 128/725 |
| 5,190,048 | 3/1993 | Wilkinson . | |
| 5,195,529 | 3/1993 | Malkamaki | 128/725 |
| 5,265,624 | 11/1993 | Bowman | 128/724 |

Primary Examiner—P. W. Echols
Attorney, Agent, or Firm—Nawrocki, Rooney & Sivertson, P.A.

[57] ABSTRACT

A plurality of flow sensors are fabricated on a single substrate. The substrate is laid out to provide the proper physical relationship of the individual sensors. The resulting multiple sensor structure may be effectively used as a respiration detector by positioning a different sensor element at each of the airflow orifices (i.e., two nostrils and mouth) of a patient. In the preferred embodiment, the sensors are thermoresistive elements, which are screened on the substrate using conductive ink. The change in temperature of the air flow in relation to the ambient at each orifice provides an indication of the flow and may be used to determine the extent of the flow. The substrate is packaged in a single piece adhesive strip which provides ease of proper attachment by the patient.

1 Claim, 7 Drawing Sheets

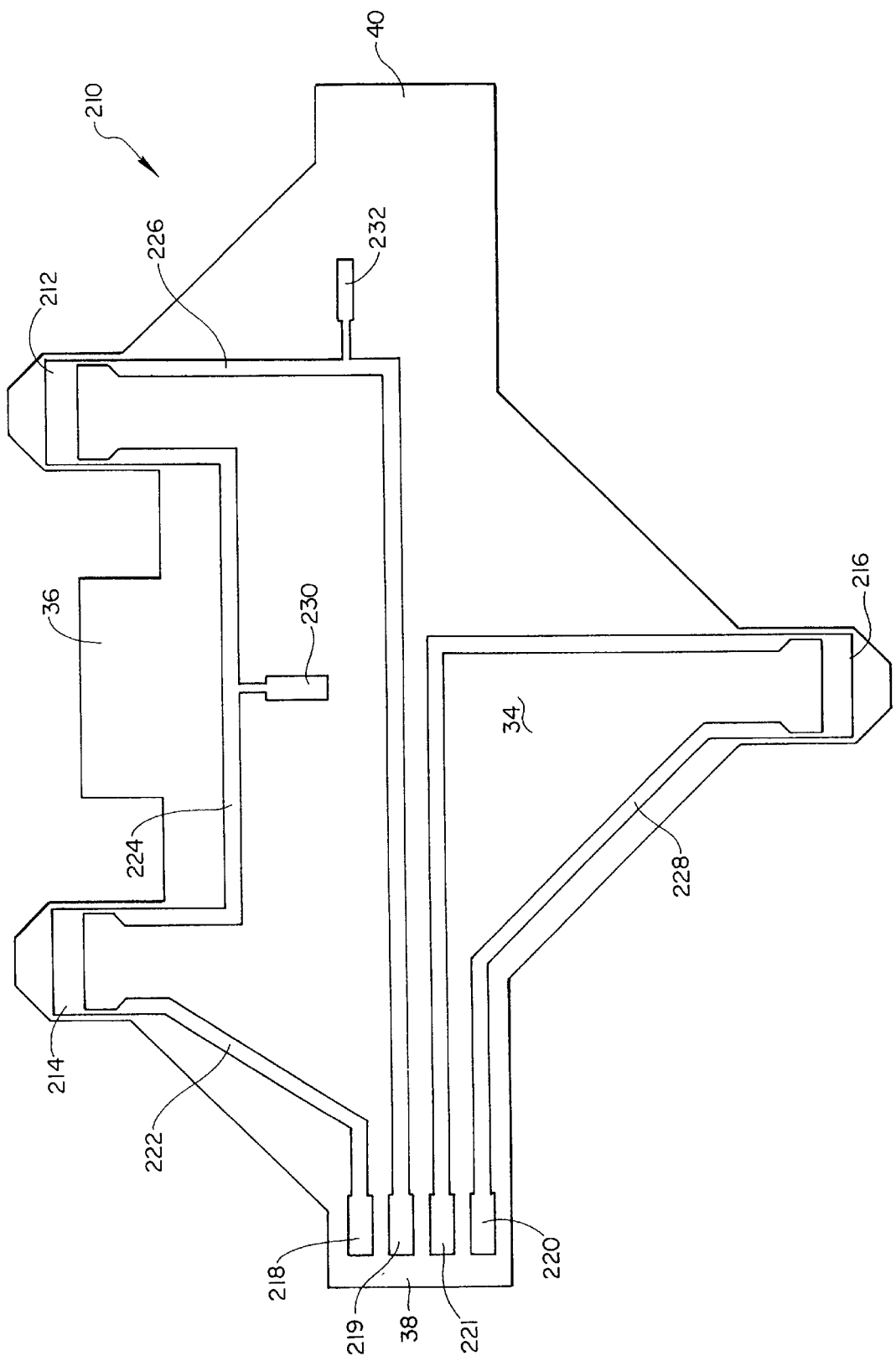

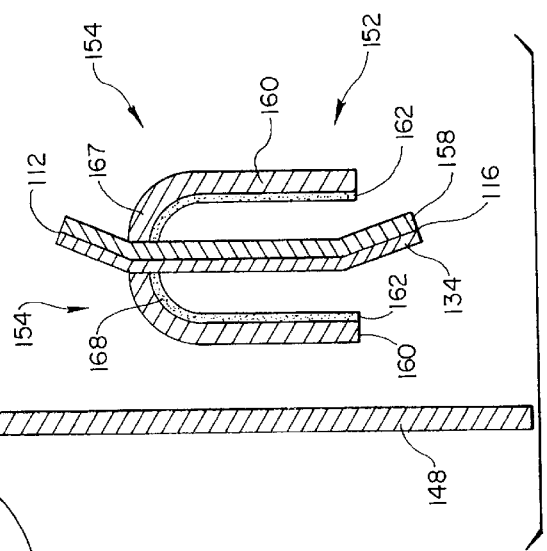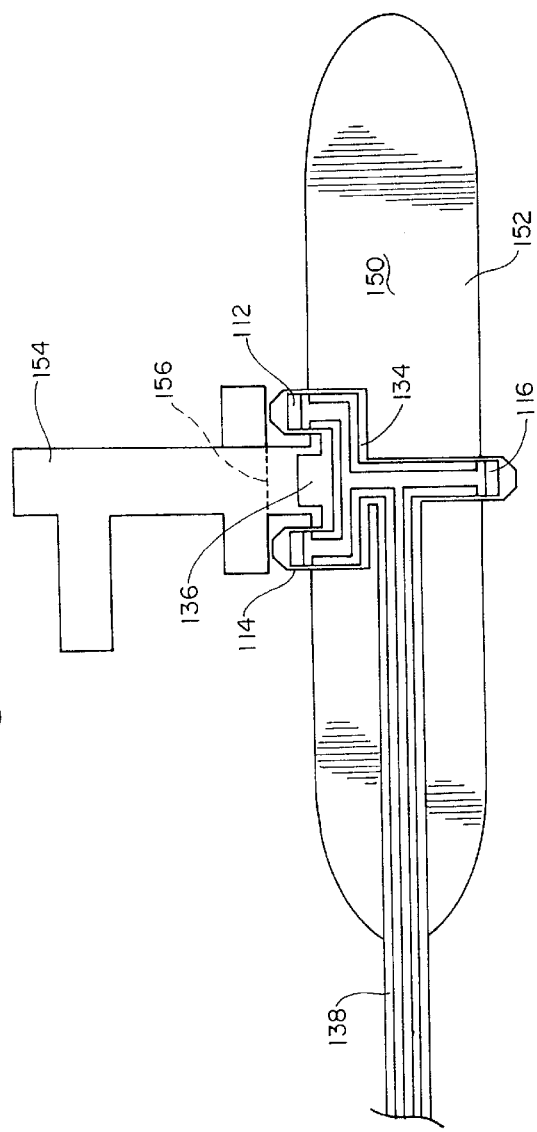

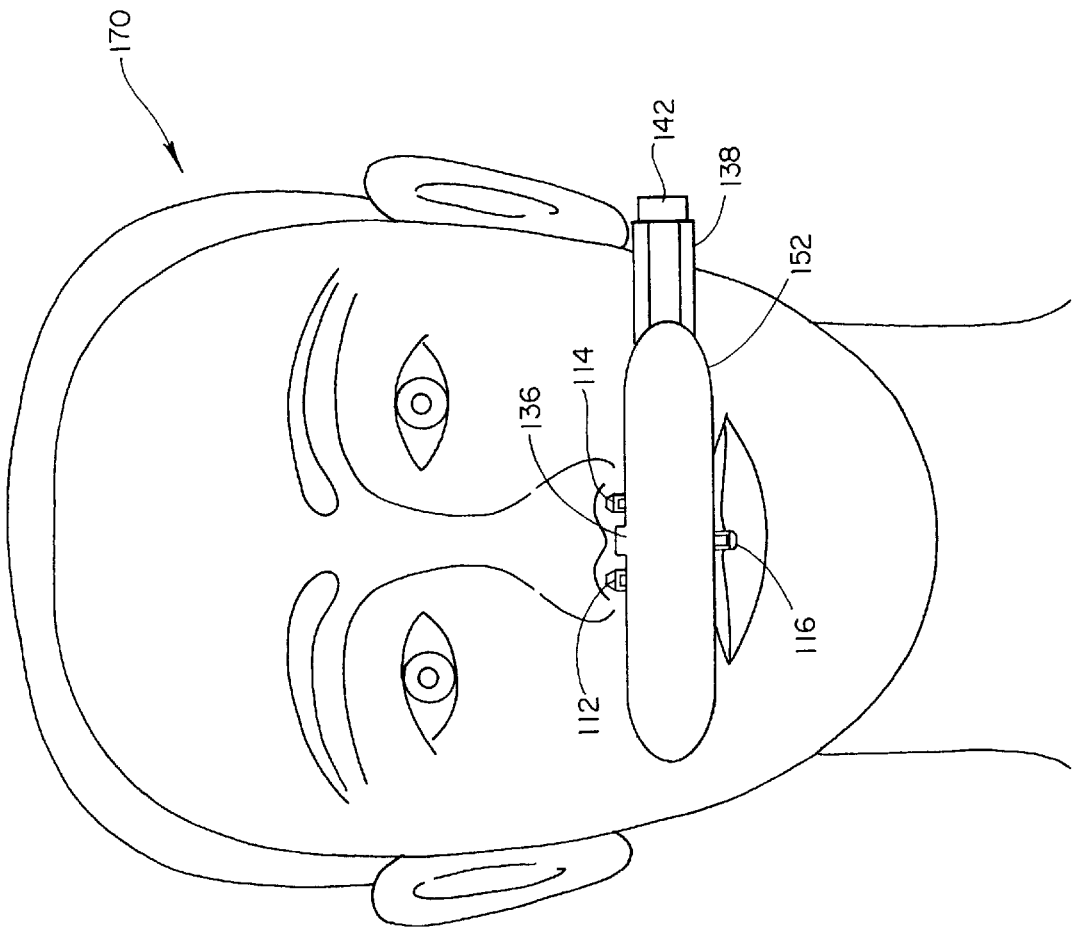
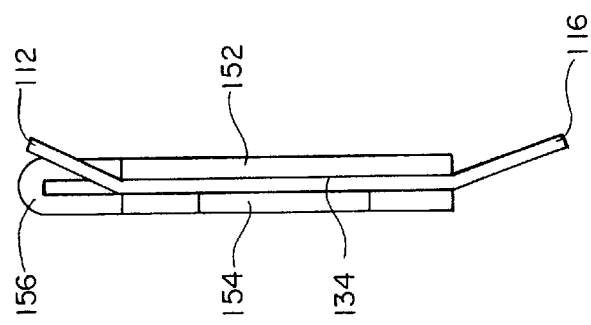

METHOD OF MAKING A RESPIRATION SENSOR

This application is a continuation of U.S. application Ser. No. 08/685,210, filed Jul. 23, 1996, now abandoned, which in turn is a continuation of U.S. application Ser. No. 08/390,929, filed Feb. 17, 1995, now abandoned, which is a continuation of U.S. application Ser. No. 08/201,045, filed Feb. 24, 1994, now abandoned, which is a continuation of U.S. application Ser. No. 07/934,725, filed Aug. 24, 1992, now abandoned, which is a divisional of U.S. application Ser. No. 07/665,552, filed Mar. 5, 1991, now U.S. Pat. No. 5,161,541.

BACKGROUND OF THE INVENTION

1. Field of the Invention

The present invention generally relates to respiration sensor technology, and more particularly, relates to respiration sensor technology for detecting abnormal breathing of a patient.

2. Description of the Prior Art

It is known in the art to employ respiration sensors to monitor patients' susceptible to sleep apnea and other disorders of the respiration system. U.S. Pat. No. 4,878,502 issued to Dietz discusses a breathing sensor employing a tubular passage in which a ball is free to move to break a beam of light. The ball is moved in response to the flow of air associated with the breathing of the patient. An optoelectric inhalation sensor using thin film deposition is discussed in U.S. Pat. No. 4,745,925 issued to Dietz.

Acoustic sensors for monitoring respiration are mentioned in U.S. Pat. No. 4,602,644 issued to DeBenedetto et al., and in U.S. Pat. No. 4,595,016 issued to Fertig et al. U.S. Pat. No. 4,366,821 issued to Wittmaier et al. shows a respiration monitoring system which preferably uses a gas sensor, and U.S. Pat. No. 4,350,166 issued to Mobarry shows a video monitor. Moisture is sensed using a sodium chloride crystal in U.S. Pat. No. 4,326,404 issued to Mehta.

U.S. Pat. No. 4,306,867 issued to Krasner shows the use of a pressure sensor. An impedance plethysmograph is employed in U.S. Pat. No. 4,289,142 issued to Kearns. The use of thermoresistive sensors is suggested in U.S. Pat. No. 3,903,876 issued to Harris, U.S. Pat. No. 3,884,219 issued to Richardson. et al., and U.S. Pat. No. 3,999,537 issued to Noiles.

SUMMARY OF THE INVENTION

The present invention overcomes the disadvantages found in the prior art by providing a plurality of sensors fabricated on a single substrate. It is advantageous to employ multiple sensing elements positioned at the various orifices which vent the upper airway of a patient. In the normal case, the three orifices are the two nostrils and the mouth. During sleep, these three orifices are used in various combinations depending upon individual habits, condition of the respiratory system (e.g. colds, etc.), and type of sleep to monitor the total respiratory effort.

The substrate is packaged within a single adhesive strip, which enables the patient to readily apply the sensor to the upper lip. The substrate is not planar placing the individual sensing elements directly into the air stream and out of contact with the skin of the patient. The sensing elements are each inclined from the plane of the substrate away from the patient.

The sensing elements may be produced using a number of technologies. In the preferred embodiment, a conductive ink having a high temperature coefficient of resistance and high resistance is applied to the substrate using a silk screening process. The individual sensing elements are interconnected in series using a conductive ink having a low resistance, and preferably low temperature coefficient of resistance. The interconnections are silk screened during a second processing step.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1B is a plan view of a conductive ink. multiple sensor system;

FIG. 5 is a partially disassembled view of the multiple sensor package;

FIG. 6 is a side sectioned view of the components of the multiple sensor package;

FIG. 7 is a side view of the multiple sensor package;

FIG. 8 is a frontal view of a patient having the multiple sensor package in place; and, FIG. 9 is a side view of a patient showing the multiple sensor package in partially sectioned form.

DETAILED DESCRIPTION OF THE PREFERRED EMBODIMENTS

Figure 1A:
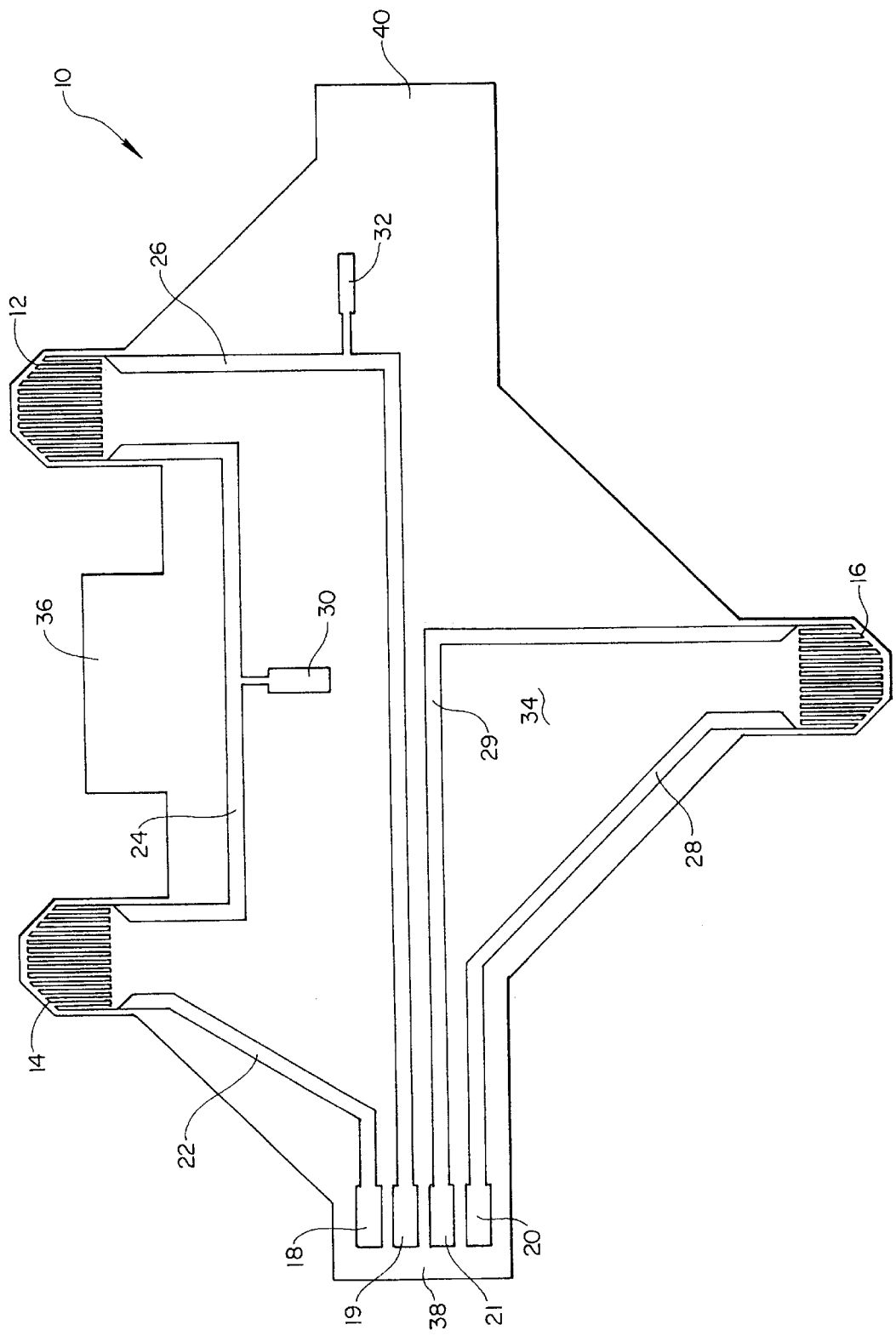
FIG. 1A is a plan view of a thin film multiple sensor system.

FIG. 1A is a plan view of a thin film multiple sensor system suitable for respiration monitoring. This embodiment employs a flexible substrate 34 of an insulating material such as a polyimide or polyester upon which individual sensing elements. 12, 14, and 16 are deposited using standard thin film deposition techniques. Alternative embodiments use conductive ink, thick film, metal foil or printed circuit board techniques. The deposited metalization layer is of a conductor, such as gold, having a high temperature coefficient of resistance, and relatively high resistance with respect to the resistance of the interconnecting conductive paths. In order to achieve a high resistance ratio between active elements and conductors, the individual sensing elements 12, 14, and 16 consist of narrow conduction loops coupled in series.

The individual sensing elements 12, 14, and 16 are electrically coupled in series by low resistance conducting paths 22, 24, 26, and 28. Connector pads 18, 19, 20 and 21 provide for electrically coupling the multiple sensor system to apparatus for measuring the resistance changes of the system. Test connector pad 30, along with connector pads 18, 19 and 20 permit testing each of the individual sensing elements.

Tabs 36, 38, and 40 are portions of substrate 34 configured to permit ease of positioning multiple sensor system 10 above the upper lip and below the nasal septum of the nose of a patient. Tab 36 may be made concave in order to aid in centering the sensor system under the nose. When substrate 34 is properly positioned, individual sensing elements 12 and 14 are located within the air stream to and from the nostrils of the patient. Similarly, individual sensing element 16 is thus positioned within the air stream of the mouth of the patient.

As a patient exhales, air heated by the patient's body impinges on the individual sensing elements 12, 14, and 16 thereby heating the narrow conduction loops and increasing the resistance of the entire multiple sensor system 10 as measured from connector pad 18 to connector pad 20 when pads 19 and 21 are shorted together. Similarly, when the patient inhales, cooler air is drawn past individual sensing elements 12, 14, and 16 causing the measurable resistance from connector pad 18 to connector pad 20 to decrease. Respiration is detected by these resistance changes. The rate and amount of the resistance change provides data concerning the nature of the respiration.

If more detailed information is desired regarding nose versus mouth breathing, connector pads 19 and 21 may be unshorted and separate measurements made from pads 18 and 19, as well as pads 20 and 21.

Bending and motion of the device does not change the overall resistance significantly because the interconnections of the active elements is of very low resistance elements. Optimal mechanical design minimizes motion artifacts from the individual sensing elements.

FIG. 1B is a plan view of an alternative embodiment of a multiple sensor system 210 employing conductive ink to fabricate the individual sensors and the conducting paths. This embodiment uses a substrate 34, which may be the same as that used for the embodiment of FIG. 1A, or in the alternative may be a clear mylar. The components of substrate 34 are as previously described.

For this embodiment, individual sensor elements 212, 214, and 216 are thermoresistive elements of a conductive ink which are silk screened on substrate 34. The conductive ink used for this purpose has a relatively high resistance and preferably a high temperature coefficient of resistance, such as Electrodag 423SS resistive carbon ink available from Acheson Cholloids Co. of Chicago, Ill. Interconnecting conducting paths 222, 224, 226, 228, and 229 are of a second type of conductive ink, such as Electrodag 427SS conductive silver ink, which is silk screened into position during a subsequent process step. This second type of conducting ink is selected to have a much lower resistance. Connector pads 218, 219, 220, and 221, along with test connector pad 230, are silk screened from the second type of conductive ink.

Operation of this embodiment is similar to the operation of the embodiment of FIG. 1A.

Figure 2:
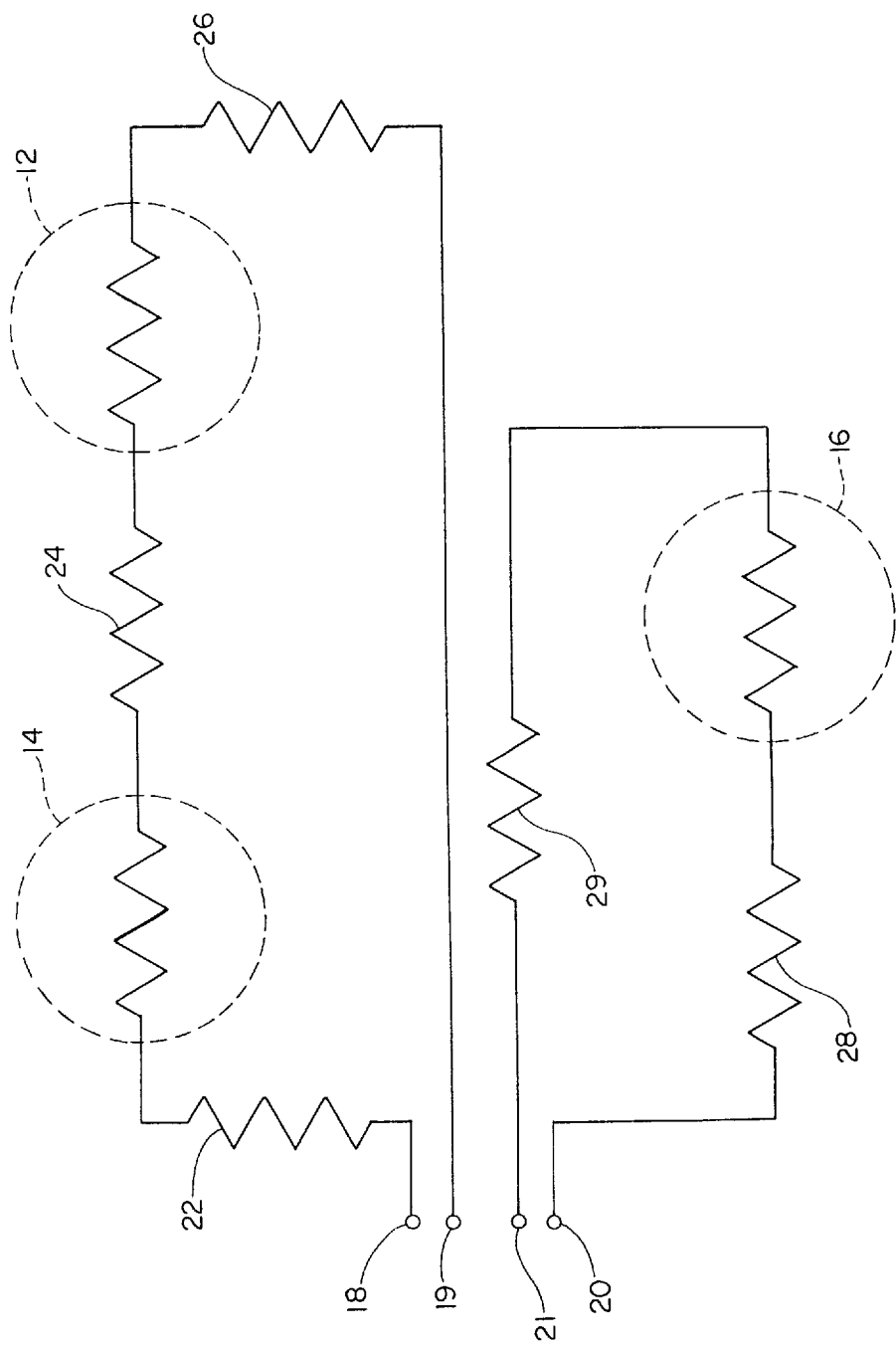
FIG. 2 is an electrical schematic diagram of a multiple sensor system.

FIG. 2 is an electrical schematic diagram of multiple sensor system 10. All referenced components are as previously described. Individual sensing elements 12, 14, and 16 are shown as variable resistance elements using the standard thermistor symbol. Conducting paths 22, 24, 26 and 28 are shown as low resistance elements reflecting their distributed resistance. An equivalent schematic diagram (not shown) could be used to depict multiple sensor system 210.

Figure 3:
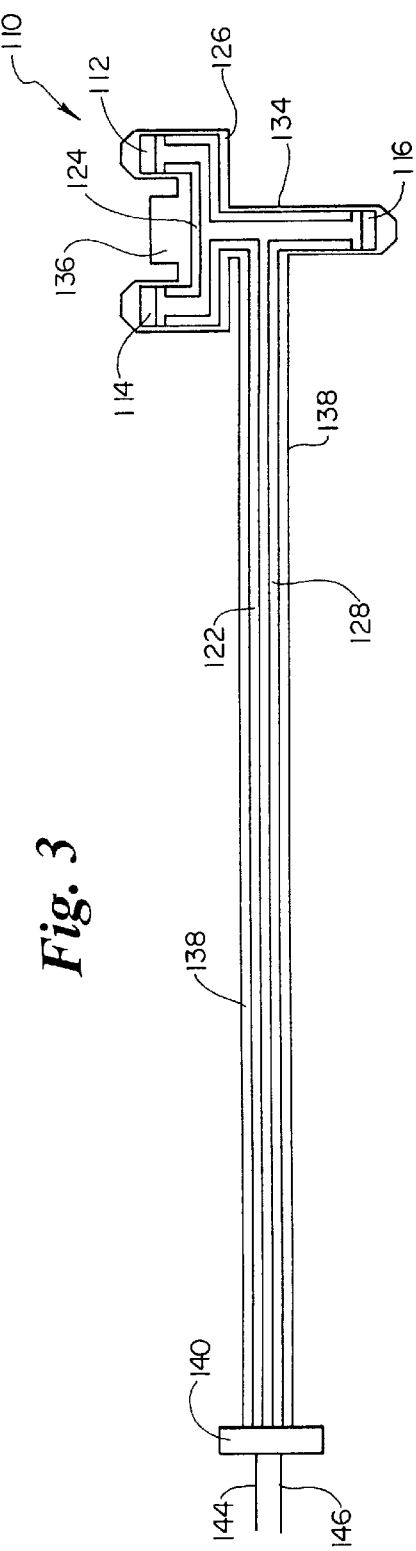
FIG. 3 is a plan view of a multiple sensor system with electrical connector.

FIG. 3 is a plan view of multiple sensor system 110, which uses an alternative method of fabrication. Substrate 134 is a flexible insulator. It is preferably of Mylar or other suitable polymer, and may be transparent or may be made of moisture resistant paper material. Substrate 134 is shaped similar to substrate 34 except that it has an extension of tab 138, for conduction paths 122 and 128, which terminate in connector assembly 142 and connector pins 144 and 146.

As with multiple sensor system 10, individual sensor elements 112 and 114 are positioned for the nostrils of the patient, and individual sensor element 116 is placed to detect flow from the mouth. Electrical conduction paths 124 and 126 couple individual sensor elements 112, 114, and 116 in series.

Multiple sensor system 110 functions in a manner similar to multiple sensor system 10 (see also FIG. 1) except that it is somewhat easier to fabricate and can use a more flexible and less expensive substrate.

Figure 4:
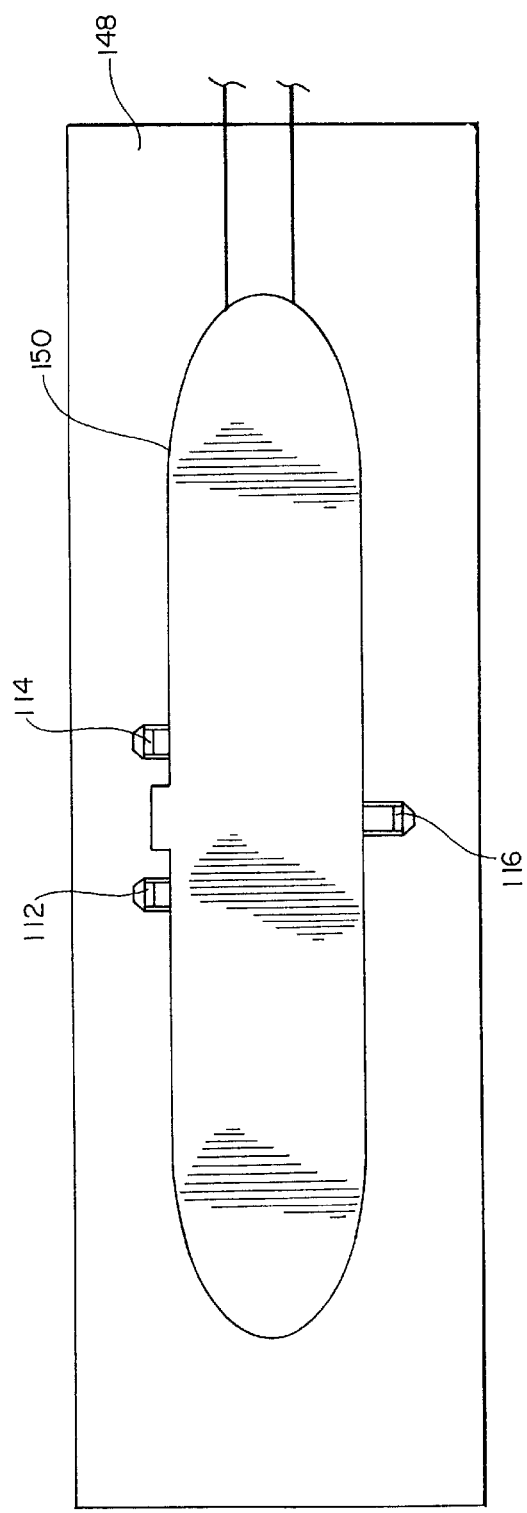
FIG. 4 is a plan view of a multiple sensor system packaged within an adhesive strip.

FIG. 4 is a plan view of multiple sensor system 110 as completely packaged. Packaging is accomplished by covering substrate 134 with adhesive strip 150 in the manner described in more detail below. Adhesive strip 150 is attached to backing substrate 148 for storage and transport. All other referenced elements are as previously described.

FIG. 5 shows the package of FIG. 4 as partially disassembled. Adhesive strip 150 is configured as shown from a single piece of single sided medical adhesive tape. Substrate 134 is adhesively affixed to the adhesive side of main portion 152 as shown. Adhesive strip 150 is folded along line 156 such that minor portion 154 also is adhesively attached to substrate 134. Adhesive strip 150 is formed to completely cover substrate 134 except for individual sensing elements 112, 114, and 116. Tab 138 can be coated with a non-conducting high dielectric material using screening techniques, or tape 150 can be extended and folded over tab 138 to protect the conductors.

FIG. 6 is a side sectioned schematic view of the major components of the fully packaged multiple sensor system 110. The view is schematic in that it is not drawn to scale for matters of illustration. All referenced components are as previously described.

Backing substrate 148 is a single layer of flexible polymer. It is used to protect the exposed surface of adhesive strip 150 during storage and transport.

Main portion 152 of adhesive strip 150 has a flexible inner substrate 160 of braided or woven polymer fibers. Adhesive layer 162 is deposited on the inner surface of substrate 160. Minor portion 154 of adhesive strip 150 is, as explained above, preferably made as a single piece with main portion 152.

FIG. 7 is a side view of the packaged multiple sensor system 110 with backing substrate 148 removed. All referenced elements are as previously described.

FIG. 8 is a frontal view of patient 170 with multiple sensor system 110 adhesively attached. The attachment is accomplished by removing major portion 152 from backing substrate 148 and placing it over the upper lip of patient 170. Because substrate 134 is flexible, multiple sensor system 110 readily conforms to the contours of the upper lip of patient 170.

As properly positioned, individual sensor elements 112 and 114 are located within the air streams of the nostrils of patient 170. Individual sensor element 116 is positioned over the air stream from the mouth of patient 170.

Figure 9:
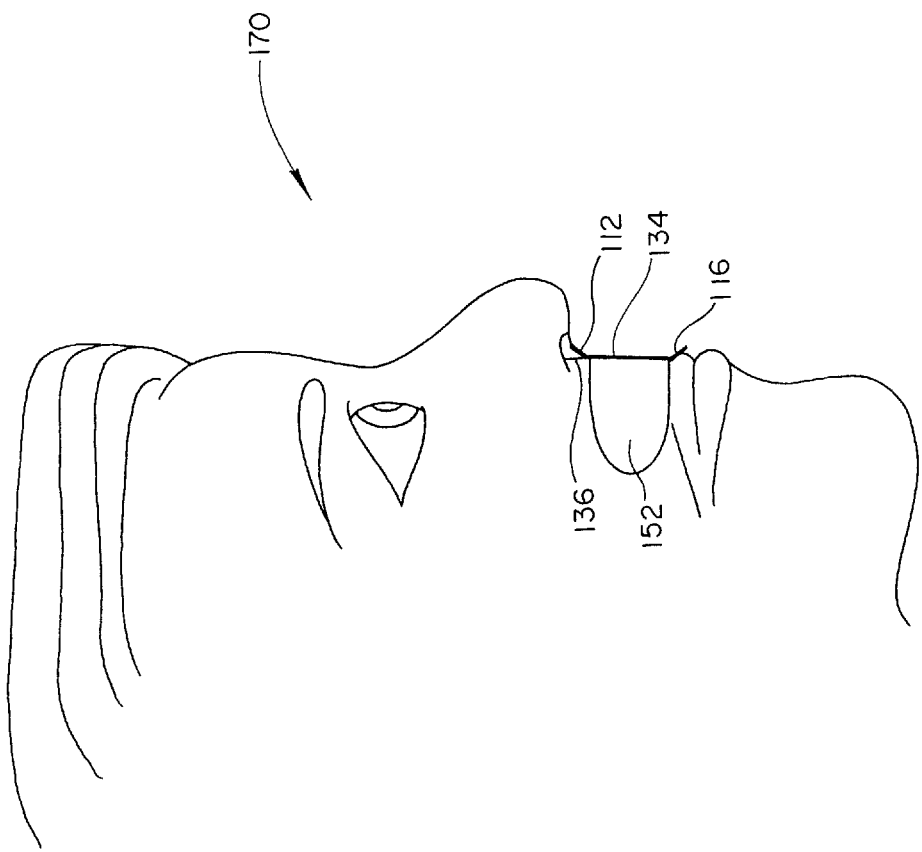

FIG. 9 is a side view of patient 170 with a sectioned view of multiple sensor system 110 to show positioning of the individual sensing elements. It can be readily seen that individual sensing elements 112, 114 (not shown), and 116 are inclined from the plane of substrate 134 away from patient 170. Positioning the individual sensing elements in this non-planar fashion places the individual sensing elements within the respective air stream and away from the skin of patient 170.

Tab 136 positions the system against the nasal septum of the nose so that individual sensing elements 112 and 114 do not occlude the nostrils. Tab 136 can be made concave to better center the system under the nose.

Having thus described the preferred embodiments of the present invention, those of skill in the art will readily appreciate that yet other embodiments may be utilized to practise the present invention within the scope of the claims hereto attached.

I claim:

1. A method of fabricating a medical sensor for determining the existence of respiration, comprising:

preparing an insulative flexible substrate;

constructing a temperature sensor by silk screening a conductive path having a first region and a second region onto said substrate;

wherein said first region comprises a first thin layer of conductive ink with a first resistance and a temperature coefficient of resistance, and said second region comprises a second thin layer of conductive ink with a second resistance lower than said first resistance, the temperature coefficient of resistance of said first region being relatively high, and wherein at least a portion of the first region forms a temperature sensing element; and forming at least first and second electrical connectors at spaced points along said conductive path for connecting the temperature sensor to an apparatus for measuring a resistance change of the conductive path in response to a temperature change of the portion of the first region forming a temperature sensing element.

* * * * *